(12) United States Patent
Hsiao et al.

(10) Patent No.: US 10,549,017 B2
(45) Date of Patent: Feb. 4, 2020

(54) SUCTION DISC

(71) Applicant: Suneetek(Xiamen) Medical Equipment Co., Ltd, Fujian (CN)

(72) Inventors: Shih-Hua Hsiao, New Taipei (TW); Chi-Yuan Chen, Keelung (TW); Bo-Cheng Huang, Taoyuan (TW)

(73) Assignee: SUNEETEK(XIAMEN) MEDICAL EQUIPMENT CO., LTD, Fujian (CN)

( * ) Notice: Subject to any disclaimer, the term of this patent is extended or adjusted under 35 U.S.C. 154(b) by 388 days.

(21) Appl. No.: 15/439,923

(22) Filed: Feb. 22, 2017

(65) Prior Publication Data

US 2018/0200417 A1    Jul. 19, 2018

(30) Foreign Application Priority Data

Jan. 13, 2017   (TW) .............................. 106101276 A

(51) Int. Cl.
*A61M 1/00*     (2006.01)
*A61F 13/00*    (2006.01)

(52) U.S. Cl.
CPC ..... *A61M 1/0088* (2013.01); *A61F 13/00055* (2013.01); *A61F 13/00068* (2013.01); *A61M 2205/3344* (2013.01)

(58) Field of Classification Search
CPC ........ A61F 13/00055; A61F 13/00068; A61M 1/0088; A61M 2205/3344
See application file for complete search history.

(56) References Cited

U.S. PATENT DOCUMENTS

2010/0106118 A1* 4/2010 Heaton ............... A61M 1/0088
                                                                                  604/319
2012/0123360 A1   5/2012 Locke et al.

FOREIGN PATENT DOCUMENTS

| CN | 101107523 A  | 1/2008  |
|----|--------------|---------|
| CN | 103379925 A  | 10/2013 |
| TW | 200950839 A1 | 12/2009 |
| TW | 201507737 A  | 3/2015  |
| TW | M528159 U    | 9/2016  |

* cited by examiner

*Primary Examiner* — Benjamin J Klein
(74) *Attorney, Agent, or Firm* — CKC & Partners Co., LLC

(57) ABSTRACT

A suction disc is configured for abutting against a dressing covering over a wound. The suction disc includes a base plate, a case, a negative pressure, a first sensing device and a second sensing device. The base plate has a first surface and a second surface opposite to each other. The first surface abuts against the dressing. The base plate has a first opening and a second opening respectively communicating with the first surface. The case has a first chamber and a second chamber. The case communicates with the second surface. The first chamber communicates with the first opening. The second chamber communicates with the second opening. The negative pressure device communicates with the second chamber. The negative pressure device provides a negative pressure to the second chamber. The first sensing device communicates with the first chamber. The second sensing device communicates with the second chamber.

8 Claims, 2 Drawing Sheets

SUCTION DISC

RELATED APPLICATIONS

This application claims priority to Taiwanese Application Serial Number 106101276 filed Jan. 13, 2017, which is herein incorporated by reference.

BACKGROUND

Technical Field

The present disclosure relates to suction discs. More particularly, the present disclose relates to suction discs utilized for negative pressure wound therapy (NPWT).

Description of Related Art

The negative pressure wound therapy (NPWT) is an adjuvant treatment for accelerating the healing of wounds, which has been becoming increasingly popular in recent years. The feature of this adjuvant treatment is to apply a negative pressure on the wound, such that the surface of the wound becomes smaller under an even distribution of the negative pressure. In addition, the body fluid can be guided and any local defect of the wound can be filled up. Moreover, excessive exudate can be removed. Furthermore, a wet but not too wet environment is provided for the closure of the wound, such that the edema of the tissue around the wound is alleviated and the growth of the granulation tissue is stimulated.

At present, negative pressure wound therapy can be broadly applied to many acute and chronic wounds in clinical treatment, including orthopedics, soft tissues, skin transplantation, pressure sores, venous leg ulcer, diabetic foot, surgical infection and postoperative wound etc. A doctor will access factors like the size, the depth, the exudate of the wound, whether the wound is infected etc., and combine with the past history of disease, the current physiological condition, the medication status and the autonomy etc., to comprehensively consider and to tell the patient if he is appropriate to receive the treatment of negative pressure wound therapy.

SUMMARY

A technical aspect of the present disclosure is to provide a suction disc, which can allow the user to grasp the degree of the absorption of the body fluid by the dressing.

According to an embodiment of the present disclosure, a suction disc configured for abutting against a dressing covering over a wound is provided. The suction disc includes a base plate, a case, a negative pressure device, a first sensing device and a second sensing device. The base plate has a first surface and a second surface opposite to each other. The first surface is configured for abutting against the dressing. The base plate further has at least one first opening and at least one second opening. The first opening and the second opening respectively communicate with the first surface. The case has at least one first chamber and at least one second chamber. The case communicates with the second surface. The first chamber communicates with the first opening. The second chamber communicates with the second opening. The negative pressure device communicates with the second chamber. The negative pressure device is configured for providing a negative pressure to the second chamber. The first sensing device communicates with the first chamber. The second sensing device communicates with the second chamber.

In one or more embodiments of the present disclosure the suction disc further includes a processor. The processor electrically connected with the first sensing device and the second sensing device.

In one or more embodiments of the present disclosure, the second sensing device communicates between the second chamber and the negative pressure device.

In one or more embodiments of the present disclosure, the negative pressure device communicates between the second chamber and the second sensing device.

In one or more embodiments of the present disclosure, the suction disc further includes a first connecting duct and a second connecting duct. The first connecting duct communicates with the negative pressure device and the second sensing device. The second connecting duct communicates with the first connecting duct and the second chamber.

In one or more embodiments of the present disclosure, the negative pressure device is a negative pressure pump.

In one or more embodiments of the present disclosure, the first sensing device is an air pressure sensing device.

In one or more embodiments of the present disclosure, the second sensing device is an air pressure sensing device.

When compared with the prior art, the above-mentioned embodiments of the present disclosure have at least the following advantages:

(1) The first sensing device communicates with the first chamber of the case, so as to sense the air pressure inside the first chamber of the case, and the second sensing device communicates with the second chamber of the case, so as to sense the air pressure inside the second chamber of the case. In this way, the user is able to grasp the air pressure in the first chamber and the air pressure in the second chamber at the same period of time. Moreover, the user is able to grasp the degree of the absorption of the body fluid by the dressing, according to the pressure difference between the air pressure in the first chamber and the air pressure in the second chamber. Consequently, according to the actual situation, the user can adjust the magnitude of the negative pressure provided by the negative pressure device to the second chamber of the case, or even replace with a new piece of dressing.

(2) Since the processor can calculate directly and provide the pressure difference between the air pressure in the first chamber and the air pressure in the second chamber, the user can more effectively grasp the degree of the absorption of the body fluid by the dressing. Consequently, according to the actual situation, the user can adjust the magnitude of the negative pressure provided by the negative pressure device to the second chamber of the case, or even replace with a new piece of dressing.

BRIEF DESCRIPTION OF THE DRAWINGS

The disclosure can be more fully understood by reading the following detailed description of the embodiments, with reference made to the accompanying drawings as follows.

DETAILED DESCRIPTION

Figure 1:
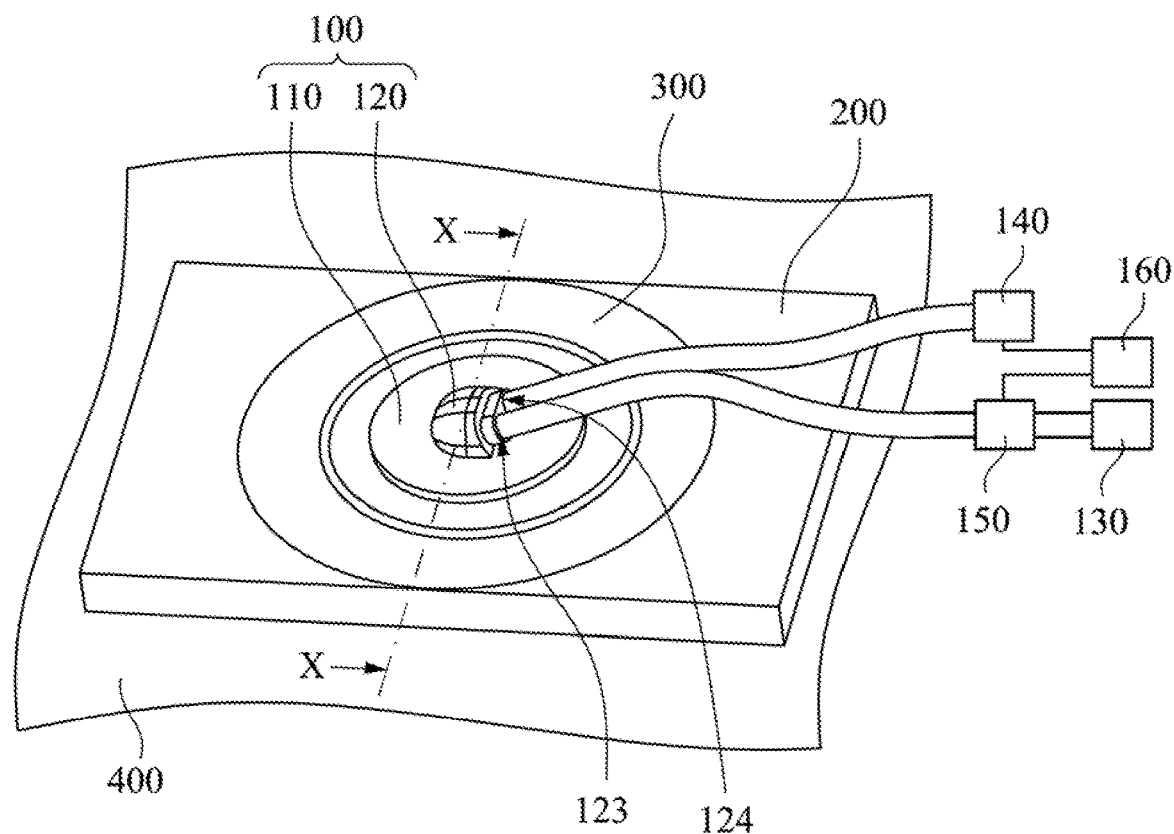
FIG. 1 is a schematic view of application of a suction disc according to an embodiment of the present disclosure.

Drawings will be used below to disclose embodiments of the present disclosure. For the sake of clear illustration, many practical details will be explained together in the description below. However, it is appreciated that the practical details should not be used to limit the claimed scope. In other words, in some embodiments of the present disclosure, the practical details are, not essential. Moreover, for the sake of drawing simplification, some customary structures and elements in the drawings will be schematically shown in a simplified way. Wherever possible, the same reference numbers are used in the drawings and the description to refer to the same or like parts.

Unless otherwise defined, all terms (including technical and scientific terms) used herein have the same meanings as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Reference is made to FIG. 1. FIG. 1 is a schematic view of application of a suction disc 100 according to an embodiment of the present disclosure. As shown in FIG. 1, a suction disc 100 is configured for being utilized in a negative pressure wound therapy (NPWT) to abutting against a dressing 200 covering over a wound 500 (please refer to FIG. 2). In practical applications, the dressing 200 is covered over the wound 500 of the patient 400. Afterwards, the suction disc 100 is disposed on a position of the dressing 200 corresponding to the wound 500. This means the dressing 200 is located between the suction disc 100 and the wound 500 of the patient 400. Furthermore, with a sticking film 300 adhered between the dressing 200 and the suction disc 100 around the wound 500, the relative position between the suction disc 100 and the dressing 200 is effectively fixed. In addition, the wound 500 is protected by the suction disc 100 and the sticking film 300, such that the wound 500 is not exposed to the air, thus reducing the chance of infection of the wound 500. In this embodiment, the suction disc 100 includes a base plate 110, a case 120, a negative pressure device 130, a first sensing device 140 and a second sensing device 150.

Figure 2:
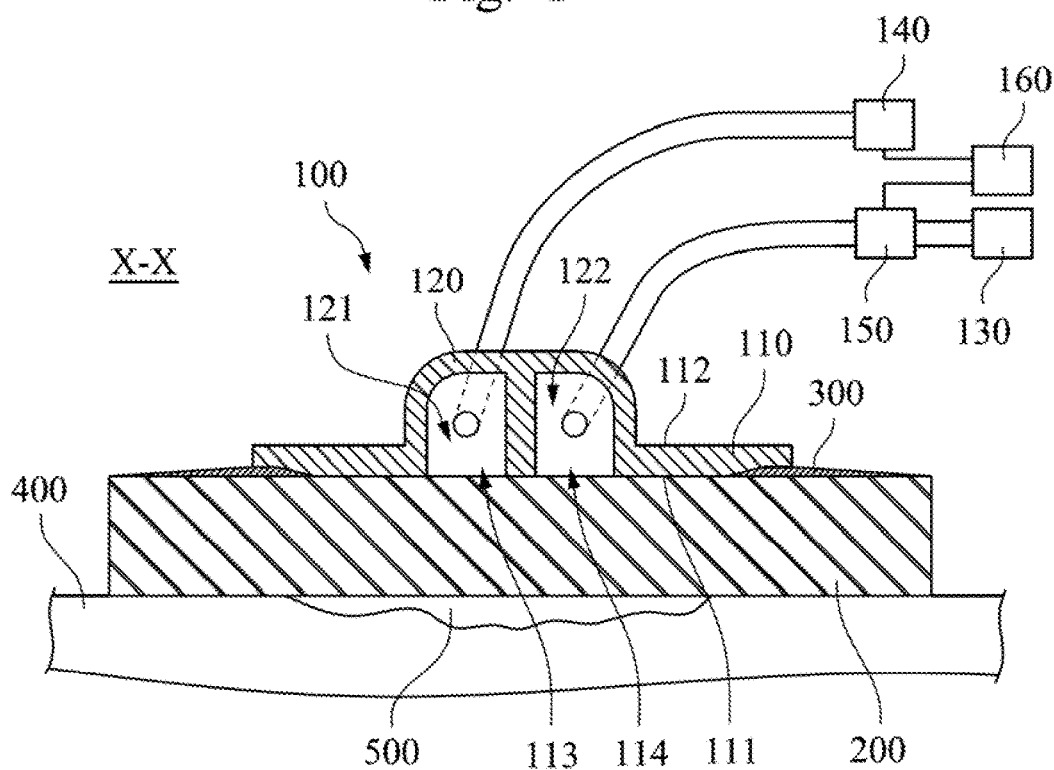
FIG. 2 is a cross-sectional view along the section line X of FIG. 1.

Please refer to FIG. 2. FIG. 2 is a cross-sectional view along the section line X of FIG. 1. As mentioned above, the suction disc 100 includes the base plate 110, the case 120, the negative pressure device 130, the first sensing device 140 and the second sensing device 150. To be more specific, as shown in FIGS. 1-2, the base plate 110 has a first surface 111 and a second surface 112 opposite to each other. The first surface 111 is configured for abutting against the dressing 200. The base plate 110 further has at least one first opening 113 and at least one second opening 114. The first opening 113 and the second opening 114 respectively communicate with the first surface 111. The case 120 has at least one first chamber 121 and at least one second chamber 122. The case 120 communicates with the second surface 112. The first chamber 121 communicates with the first opening 113. The second chamber 112 communicates with the second opening 114. The negative pressure device 130 communicates with the second chamber 122. The negative pressure device 130 is configured for providing a negative pressure to the second chamber 122. Moreover, the first sensing device 140 communicates with the first chamber 121, and the second sensing device 150 communicates with the second chamber 122.

In practical applications, as mentioned above, the negative pressure device 130 communicates with the second chamber 122 of the case 120. Moreover, the negative pressure device 130 is configured for providing a negative pressure to the second chamber 122 of the case 120. In this embodiment, the negative pressure device 130 can be a negative pressure pump, which generates a suction force to the second chamber 122 of the case 120. Thus, negative pressure device 130 generates a regional negative pressure to the second chamber 122 of the case 120. In the process of treatment, exudation from the wound 500 occurs continuously. The regional negative pressure generated by the suction disc 100 in the second chamber 122 of the case 120 is able to suck the infected substances and the excessive tissue exudate from the wound 500, so as to maintain the wettability of the wound 500 reduce the range of edge of the wound 500, and increase the flow volume of blood of the capillaries in the vicinity. Furthermore, the cells and thus the angiogenesis are stimulated by the mechanical stress generated by the dressing 200. Thus, the growth of the granulation tissue is promoted. All these mechanisms work together to speed up the healing process of the wound 500.

In addition, as mentioned above, the first sensing device 140 communicates with the first chamber 121 of the case 20. Moreover, in this embodiment, the first sensing device 140 is an air pressure sensing device, so to sense the air pressure inside the first chamber 121 of the case 120. To be more specific, the dressing 200 can be a porous material. This means that the first chamber 121 and the second chamber 122 can communicate with each other through the dressing 200. In other words, when the negative pressure device 130 provides a negative pressure to the second chamber 122 of the case 120, the air pressure inside the second chamber 122 of the case 120 is lower than the first chamber 121. Thus, the air in the first chamber 121 of the case 120 will flow to the second chamber 122 through the dressing 200. However, after the exudate from the wound 500 is gradually absorbed into the dressing 200 the porous structure of the dressing 200 may be blocked, such that the process that the air in the first chamber 121 of the case 120 flows to the second chamber 122 through the dressing 200 gradually becomes more difficult. As a result, the air pressure inside the first chamber 121 of the case 120 is also varied. With the variation of the air pressure inside the first chamber 121 being sensed by the first sensing device 140, the user can grasp the degree of the absorption of the body fluid by the dressing 200. Consequently, according to the actual situation, the user can adjust the magnitude of the negative pressure provided by the negative pressure device 130 to the second chamber 122 of the case 120, or even replace with a new piece of dressing 200.

On the other hand, as mentioned above, the second sensing device 150 communicates with the second chamber 122 of the case 120. Furthermore, in this embodiment, the second sensing device 150 is also an air pressure sensing device, so as to sense the air pressure inside the second chamber 122 of the case 120. In this way, the user is able to grasp the air pressure in the first chamber 121 and the air pressure in the second chamber 122 at the same, period of time. Moreover, the user is able to grasp the degree of the absorption of the body fluid by the dressing 200, according to the pressure difference between the air pressure in the first chamber 121 and the air pressure in the second chamber 122. Consequently, according to the actual situation, the user can adjust the magnitude of the negative pressure provided by the negative pressure device 130 to the second chamber 122 of the case 120, or even replace with a new piece of dressing 200. To be more specific, the air pressure inside the second chamber 122 of the case 120 as sensed by the second sensing device 150, is substantially equal to or similar to the negative pressure provided by the negative pressure device 130 to the second chamber 122 of the case 120.

In addition, in order to enhance the convenience of the operation of the suction disc 100 by the user, in this embodiment, the suction disc 100 further includes a processor 160. As shown in FIGS. 1-2, the processor 160 is electrically connected with the first sensing device 140 and the second sensing device 150. The processor 160 can calculate directly the pressure difference between the air pressures respectively sensed by the first sensing device 140 and the second sensing device 150, i.e., the pressure difference between the air pressure in the first chamber 121 and the air pressure in the second chamber 122. Therefore, the user can more effectively grasp the degree of the absorption of the body fluid by the dressing 200. Consequently, according to the actual situation, the user can adjust the magnitude of the negative pressure provided by the negative pressure device 130 to the second chamber 122 of the case 120, or even replace with a new piece of dressing 200.

In practical applications, as shown in FIGS. 1-2, the second sensing device 150 communicates between the second chamber 122 of the case 120 and the negative pressure device 130. However, this does not intend to limit the present disclosure.

Figure 3:
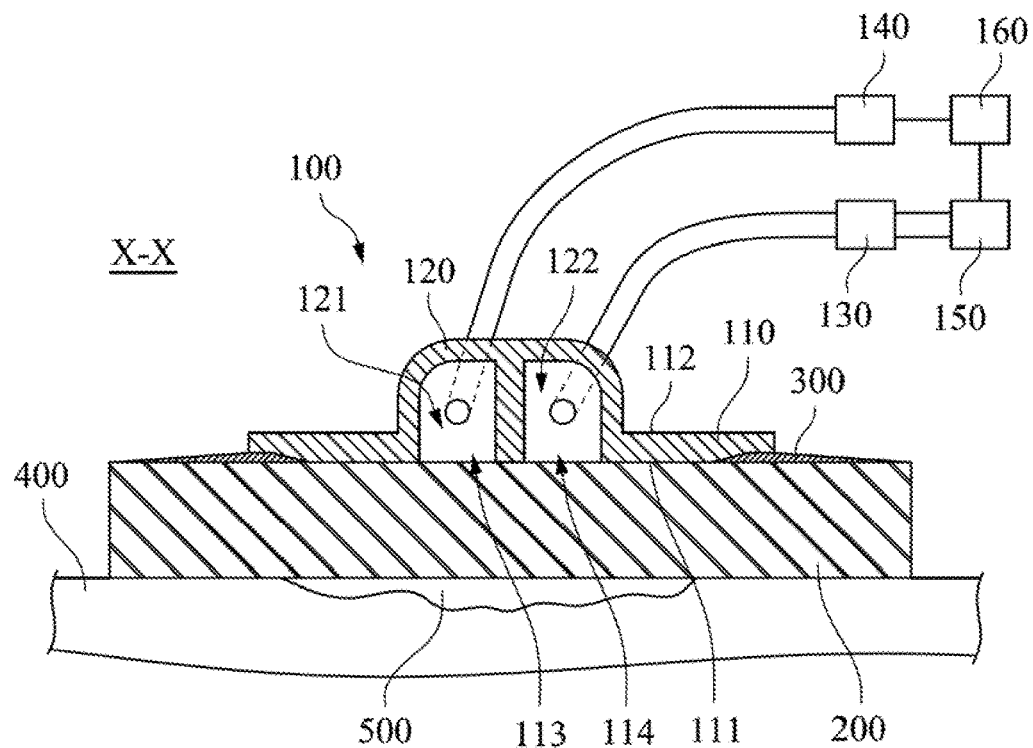
FIG. 3 is a schematic view of application of a suction disc according to another embodiment of the present disclosure.

Please refer to FIG. 3. FIG. 3 is a schematic view of application of a suction disc 100 according to another embodiment of the present disclosure. In this embodiment, according to the actual situation, as shown in FIG. 3, the negative pressure device 130 communicates between the second chamber 122 of the case 120 and the second sensing device 150, and the second sensing device 150 senses the negative pressure provided by the negative pressure device 130 to the second chamber 122. In this way, the application of the suction disc 100 becomes more flexible.

Figure 4:
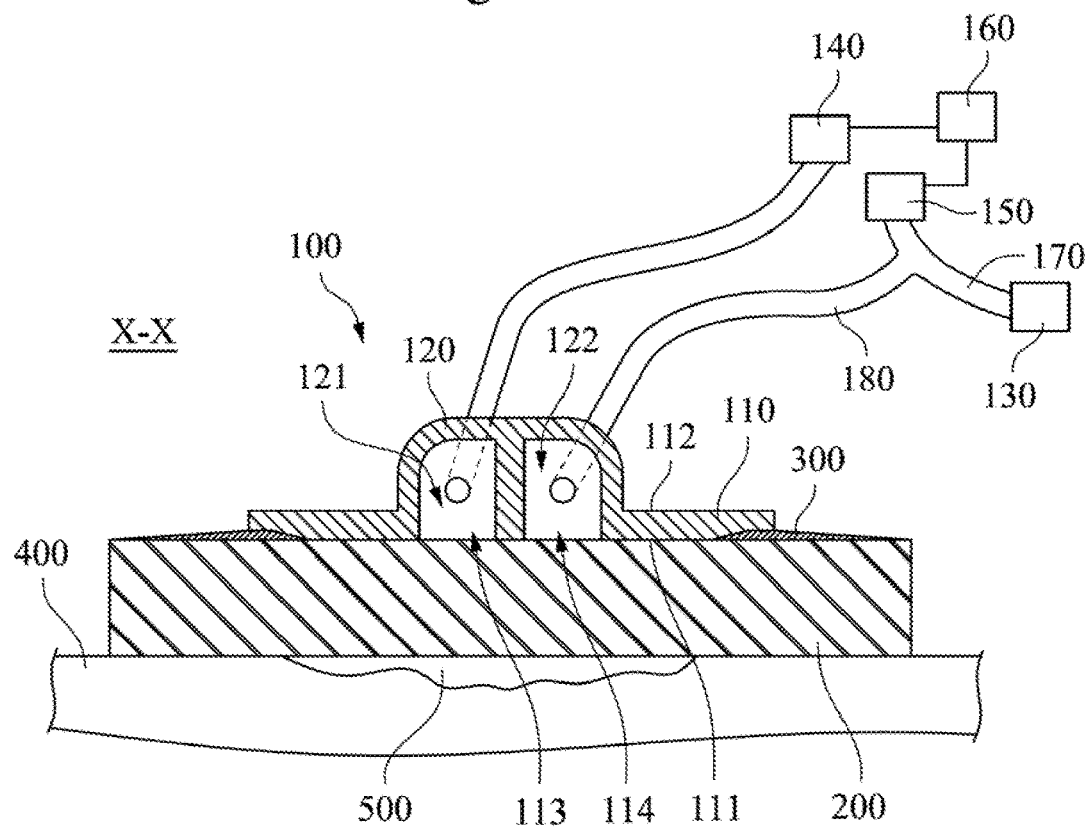
FIG. 4 is a schematic view of application of a suction disc according to a further embodiment of the present disclosure.

Please refer to FIG. 4. FIG. 4 is a schematic view of application of a suction disc 100 according to a further embodiment of the present disclosure. In this embodiment, according to actual situation the suction disc 100 further includes a first connecting duct 170 and a second connecting duct 180. As shown in FIG. 4, the first connecting duct 170 communicates with the negative pressure device 130 and the second sensing device 150, and the second connecting duct 180 communicates with the first connecting duct 170 and the second chamber 122 of the case 120. In this way, the configuration of the relative positions of the negative pressure device 130, the second sensing device 150 and the case 120 becomes more flexible.

In conclusion, when compared with the prior art, the aforementioned embodiments of the present disclosure have at least the following advantages.

(1) The first sensing device communicates with the first chamber of the case, so as to sense the air pressure inside the first chamber of the case, and the second sensing device communicates with the second chamber of the case, so as to sense the air pressure inside the second chamber of the case. In this way, the user is able to grasp the air pressure in the first chamber and the air pressure in the second chamber at the same period of time. Moreover, the user is able to grasp the degree of the absorption of the body fluid by the dressing, according to the pressure difference between the air pressure in the first chamber and the air pressure in the second chamber. Consequently, according to the actual situation, the user can adjust the magnitude of the negative pressure provided by the negative pressure device to the second chamber of the case, or even replace with a new piece of dressing.

(2) Since the processor can calculate directly and provide the pressure difference between the air pressure in the first chamber and the air pressure in the second chamber, the user can more effectively grasp the degree of the absorption of the body fluid by the dressing. Consequently, according to the actual situation, the user can adjust the magnitude of the negative pressure provided by the negative pressure device to the second chamber of the case, or even replace with a new piece of dressing.

Although the present disclosure has been described in considerable detail with reference to certain embodiments thereof, other embodiments are possible. Therefore the spirit and scope of the appended claims should not be limited to the description of the embodiments contained herein.

It will be apparent to the person having ordinary skill in the art that various modifications and variations can be made to the structure of the present disclosure without departing from the scope or spirit of the present disclosure. In view of the foregoing, it is intended that the present disclosure cover modifications and variations of the present disclosure provided they fall within the scope of the following claims.

What is claimed is:

1. A suction disc configured for abutting against a dressing covering over a wound, the suction disc comprising:
   a base plate having a first surface and a second surface opposite to each other, the first surface being configured for abutting against the dressing, the base plate further having at least one first opening and at least one second opening, the first opening and the second opening respectively communicating with the first surface;
   a case having at least one first chamber and at least one second chamber, the case communicating with the second surface, the first chamber communicating with the first opening, and the second chamber communicating with the second opening, wherein the first chamber and the second chamber are spatially isolated when the first opening and the second opening are sealed by the dressing;
   a negative pressure device communicating with the second chamber, the negative pressure device being configured for providing a negative pressure to the second chamber;
   a first sensing device communicating with the first chamber;
   a second sensing device communicating with the second chamber;
   a first chamber duct which forms a single enclosed space and extends between the first chamber and the first sensing device, wherein the first sensing device communicates with the first chamber directly via the first chamber duct; and
   a second chamber duct which forms a single enclosed space and extends between the second chamber and both the second sensing device and the negative pressure device, wherein the second sensing device communicates with the second chamber directly via the second chamber duct or directly via the negative pressure device and the second chamber duct, and the negative pressure device communicates with the second chamber directly via the second chamber duct or directly via the second sensing device and the second chamber duct, wherein the second chamber duct has a first end connected to both of the second sensing device and the negative pressure device, and a second end connected to the second chamber, and in a direction from the first end to the second end, the order of connection among the second sensing device, the negative pressure device, and the second chamber is the negative pressure device, the second sensing device, and the second chamber, or the second sensing device, the negative pressure device, and the second chamber.

2. The suction disc of claim 1, further comprising a processor electrically connected with the first sensing device and the second sensing device.

3. The suction disc of claim 1, wherein the second sensing device communicates between the second chamber and the negative pressure device.

4. The suction disc of claim 1, wherein the negative pressure device communicates between the second chamber and the second sensing device.

5. The suction disc of claim 1, further comprising:

a first connecting duct communicating with the negative pressure device and the second sensing device; and a second connecting duct communicating with the first connecting duct and the second chamber.

6. The suction disc of claim 1, wherein the negative pressure device is a negative pressure pump.

7. The suction disc of claim 1, wherein the first sensing device is an air pressure sensing device.

8. The suction disc of claim 1, wherein the second sensing device is an air pressure sensing device.

* * * * *